US006054147A

United States Patent [19]
Barclay et al.

[11] Patent Number: 6,054,147
[45] Date of Patent: Apr. 25, 2000

[54] METHOD FOR INCREASING THE INCORPORATION EFFICIENCY OF OMEGA-3 HIGHLY UNSATURATED FATTY ACID IN POULTRY MEAT

[75] Inventors: William R. Barclay, Boulder; Jesus Ruben Abril, Westminster, both of Colo.

[73] Assignee: OmegaTech, Inc., Boulder, Colo.

[21] Appl. No.: 09/134,504

[22] Filed: Aug. 14, 1998

Related U.S. Application Data

[60] Provisional application No. 60/055,765, Aug. 14, 1997.

[51] Int. Cl.$^7$ ............................. A01K 29/00; A23L 29/00
[52] U.S. Cl. ................................ 426/2; 426/53; 426/601; 426/635; 426/807
[58] Field of Search ................................ 426/2, 53, 601, 426/635, 807

[56] References Cited

U.S. PATENT DOCUMENTS

| | | | |
|---|---|---|---|
| 2,879,162 | 3/1959 | Baldini et al. | 99/4 |
| 4,918,104 | 4/1990 | Weiss et al. | 514/560 |
| 5,012,761 | 5/1991 | Oh | 119/6.8 |
| 5,130,242 | 7/1992 | Barclay | 435/134 |
| 5,133,963 | 7/1992 | Ise | 424/94.61 |
| 5,415,879 | 5/1995 | Oh | 426/2 |

OTHER PUBLICATIONS

Barlow and Pike, "Humans, animals benefit from omega–3 polyunsaturated fatty acids," *Feedstuffs*, May 13, 1991, pp. 18–26.
McLeod, "Nutritional Factors Influencing Carcase Fat in Broilers—A Review," *Worlds Poultry Science Journal*, 1981, 37, 194–200.
Nir, "Performance of Broilers Fed Diets Supplemented with 1.5% Soybean or Redfish Oil," *Poultry Sci. Suppl.*, Abstract of Papers, 1990, 69(1), p. 99.
Opstvedt, "Influence of Residual Lipids on Nutritive Value of Fish Meal," *Acta Agric. Scand.*, 1973, 23, pp. 217–224.
Cruickshank, Poultry Nutritional Section, Animal Nutritional Institute, School of Agriculture, Cambridge; "CXXXVI. Studies in Fat Metabolism in the Fowl. I. The Composition of the Egg Fat and Depot Fat of the Fowl as Affected by the Ingestion of Large Amounts of Different Fats," *Biochemical Journal*, 1934, 28, pp. 965–977.
Leskanich and Noble, "Manipulation of the n–3 polyunsaturated fatty acid composition of avian eggs and meat," *World's Poultry Science Journal*, 1997, 53, 155–183.
Edwards and May, "Studies with Menhaden Oil in Practical–Type Broiler Rations," *Poultry Sci.*, 1965, 44, 685–689.
Miller et al., "Effect of Feeding and Withdrawal of Menhaden Oil on the w3 and w6 Fatty Acid Content of Broiler Tissues," *J. Food Sci.*, 1969, 34, 136–141.
Dansky, "The Growth Promoting Properties of Menhaden Fish Oil as Influenced by Various Fats," *Poultry Sci.*, 1962, 41, 1352–1354.
Marion adn Woodroof, "The Fatty Acid Composition of Breast, Thigh, and Skin Tissues of Chicken Broilers as Influenced by Dietary Fats," *Poultry Sci.*, 1963, 42, 1202–1207.
Ajuyah et al., "Studies on canola seed in turkey grower diet: Effects on w–3 fatty acid composition of breast meat, breast skin and selected organs," *Can. J. Anim. Sci.*, 1993, 73, 177–181.
Nwokolo and Sim, "w–3 Fatty Acid Enrichment of Broiler and Layer Tissues, and Egg Yolk by Feeding Flax and Canola Seed Diets," *Poultry Sci.* vol. 68: Suppl.; 1990, p. 106, Abstract, 78th Ann. Poultry Sci. Assn. Mtg.
Hulan et al., "The Broiler Chicken as an Alternative to Fish and Shellfish as a Dietary Source of Eicosapentaenoic Acid," *Poultry Sci.* vol. 65 Suppl., p. 60, Abstract, 75th Ann. Meeting.
Edwards, Jr. and May, "Studies with Menhaden Oil in Practical–Type Broiler Rations," *Poultry Sci.*, 1965, 44, 685–688.
Miller et al., "Dietary Effect of Menhaden–Oil Ethyl Esters on the Fatty Acid Pattern of Broiler Muscle Lipids," *Poultry Sci.*, 1967, 46, 438–444.
Sell et al., "Fatty Acid Composition of Egg Yolk and Adipose Tissue as Influenced by Dietary Fat and Strain of Hen," 1968, 47, 1296–1302.
Ajuyah et al., "Dietary Antioxidants and Storage Affect Chemical Characteristics of w–3 Fatty Acid Enriched Broiler Chicken Meats," *J. Food Sci.*, 1993, 58(1), 43–46.
Cherian and Sim, "Effect of Feeding Full Fat Flax and Canola Seeds to Laying Hens on the Fatty Acid Composition of Eggs, Embryos, and Newly Hatched Chicks," *Poultry Sci.*, 1991, 70, 917–922.
Galvin et al., "Effect of dietary oil quality and α–tocopherol supplementation on the oxidative stability of broiler tissues," *Proc. Nutrition Soc.*, 1994, 53(2), 13A.
Miller et al., "Dietary Effect of Menhaden–Oil Ethyl Esters on the Fatty Acid Pattern of Broiler Muscle Lipids," *Poultry Sci.*, 1967, 46, 438–444.
Miller and Robisch, "Comparative Effect of Herring, Menhaden, and Safflower Oils on Broiler Tissues Fatty Acid Composition and Flavor," *Poultry Sci.*, 1969, 48, 2146–2157.
Hulan and Proudfoot, "Replacement of Soybean Meal in Chicken Broiler Diets by Rapeseed Meal and Fish Meal Complementary Sources of Dietary Protein," *Can. J. Anim. Sci.*, 1981, 61, 999–1004.
Miller et al., "Effect of Refined Menhaden Oils on the Flavor and Fatty Acid Composition of Broiler Flesh," *J. Food Sci.*, 1967, 32, 342–345.

(List continued on next page.)

*Primary Examiner*—Anthony J. Weier
*Attorney, Agent, or Firm*—Sheridan Ross P.C.

[57] ABSTRACT

A feeding regime for increasing the incorporation efficiency of omega-3 HUFAs in poultry meat is provided. Specifically, the poultry is fed a higher amount of omega-3 HUFAs in the late phase of poultry's production period than in the early phase.

73 Claims, No Drawings

OTHER PUBLICATIONS

Phetteplace et al., "Effects of Dietary n–6 and n–3 Fatty Acids on Lipid Metabolism in Two Genetic Lines of Broilers," *Poultry Sci.*, vol. 68: Suppl. 1: 1990, p. 114, Abstract, 78th Ann. Poultry Sci. Assn. Mtg.

n–3 News Unsaturated Fatty Acids and Health, Mar. 1988, vol. III, No. 1, pp. 1–4.

Nir, "Performance of Broilers Fed Diets Supplemented with 1.5% Soybean or Redfish Oil," *Poultry Science (Suppl)*, 1990, 69(1), 99.

Phetteplace and Watkins, "Dietary n–3 Fatty Acids Lowered Plasma Triacylglycerols in Male Broilers," *Poultry Sci.*, vol. 68: Suppl. 1: 1990, p. 114, Abstract, 78th Ann. Poultry Sci. Assn. Mtg.

Yau et al., "Enrichment of Selected Fatty Acids in Broiler Tissues," *Poultry Sci.*, vol. 68: Suppl. 1: 1990, p. 162, Abstract, 78th Ann. Poultry Sci. Assn. Mtg.

Hulan et al., "Omega–3 Fatty Acid Levels and General Performance of Commercial Broilers Fed Practical Levels of Redfish Meal," *Poultry Sci.*, 1989, 68, 153–162.

Krogdahl, "Digestion and Absorption of Lipids in Poultry," *J. Nutrition*, 1985, 115, 675–685.

Miller et al., "Effect of Dietary Fat on Tissue Fat and Plasma Cholestrol Level in Broilers," *Poultry Sci.*, 1962, 41, 970–974.

Neudoerffer et al., "Effects of dietary fish oil on the composition and stability of turkey depot fat," *Br. J. Nutr.*, 1966, 20, 581–594.

Opstvedt, "Influences of Residual Lipids on the Nutritive Value of Fish Meal," *Acta Agri. Scand.*, 1973, 23, 200–208.

Opstvedt et al., "Influence of Residual Lipids on the Nutritive Value of Fish Meal," *Acta Agri. Scand.*, 1970, 20, 185–193.

Waldroup et al., "Fish Meal Studies. 1. Effects of Levels and Sources on Broiler Growth Rate and Feed Efficiency," *Poultry Sci.*, 1965, 44, 1012–1016.

Fry et al., "Fish Meal Studies. 2. Effects of Levels and Sources on "Fishy Flavor" in Broiler Meat," *Poultry Sci.*, 1965, 44, 1016–1019.

Wheeler et al., "Fatty Acid Distribution in Egg Yolk as Influenced by Type and Level of Dietary Fat," *J. Nutrition*, 1959, 69, 253–257.

Mokady et al., "Protein Nutritive Value of Several Microalgae Species for Young Chickens and Rats," *Algae Biomass*, Shelef and Soeder, eds., Elsevier/North–Holland Biomedical Press, 1980, pp. 655–660.

Walz et al., "Studies on Some Nutritive Effects of the Green Algae *Scenedesmus acutus* with Pigs and Broilers," *Algae Biomass*, Shelef and Soeder, eds., Elsevier/North–Holland Biomedical Press, 1980, pp. 733–744.

Combs, "Algae (Chlorella) as a Source of Nutrients for the Chicks," *Science*, 1952, 116, 453–454.

Leveille et al., "Protein Value and the Amino Acid Deficiencies of Various Algae for Growth of Rats and Chicks," *J. Nutrition*, 1962, 76, 423–428.

Yannai et al., "The Safety of Several Algae Grown on Wastewater as a Feedstuff for Broilers," *Arch. Hydrobiol. Beih. Ergebn. Limmol.*, 1978, 11, 139–149.

Mokady et al., "Nutritional Evaluation of the Protein of Several Algae Species for Broilers," *Arch. Hydrobiol. Beih. Ergebn. Limmol.*, 1978, 11, 89–97.

Edwards, Jr. et al., "Carcass Composition Studies. 1. Influences of Age, Sex and Type of Dietary Fat Supplementation on Total Carcass and Fatty Acid Composition," *Poultry Sci.*, 1972, 52, 934–948.

Couch et al., "Effect of Diet on Triglyceride Structure and Composition of Egg Yolk Lipids," *Lipids*, 1973, 8, 385–392.

Hulan et al., "The Effects of Different Dietary Fat Sources on General Performance and Carcass Fatty Acid Composition of Broiler Chickens," *Poultry Sci.*, 1984, 63, 324–332.

"CRC Handbook of Microalgal Mass Culture," Richmond, A. ed., CRC Press, Inc., Boca Raton, Florida, 1986, pp. 344–398.

Lipstein et al., "The Nutritional Value of Algae for Poultry. Dried Chlorella in Broiler Diets," *Br. Poultry Sci.*, 1980, 21, 9–21.

Lipstein et al., "The Nutritional and Economic Value of Algae for Poultry," *Algae Biomass*, Shelef and Soeder, eds., Elsevier/North–Holland Biomedical Press, 1980, pp. 667–685.

Reiser, "The Syntheses and Interconversions of Polyunsaturated Fatty Acids by the Laying Hen," *J. Nutrition*, 1951, 44, 159–175.

Lipstein et al., "The Nutritional Value of Algae for Poultry. Dried Chlorella in Layer Diets," *Br. Poultry Sci.*, 1980, 21, 23–27.

Hargis, "Designing Eggs for the Health Conscious Consumer," *Egg Industry*, Nov./Dec. 1992, 24–30.

Navarro et al., "Influence of Dietary Fish Meal on Egg Fatty Acid Composition," *J. Sci. Fd. Agric.*, 1972, 23, 1287–1292.

Miller et al., "Dietary Effect of Menhaden–Oil Ethyl Esters on the Fatty Acid Pattern of Broiler Muscle Lipids," *Poultry Sci.*, 1967, 46, 438–444.

METHOD FOR INCREASING THE INCORPORATION EFFICIENCY OF OMEGA-3 HIGHLY UNSATURATED FATTY ACID IN POULTRY MEAT

CROSS-REFERENCE TO RELATED APPLICATIONS

This application claims the benefit of U.S. Provisional Application No. 60/055,765, filed Aug. 14, 1997.

FIELD OF THE INVENTION

The present invention relates to a method for increasing the amount of omega-3 highly unsaturated fatty acids in poultry meat by feeding the poultry a higher amount of omega-3 highly unsaturated fatty acids in the later phase of its production period than the early phase.

BACKGROUND OF THE INVENTION

Omega-3 (n-3) highly unsaturated fatty acids (HUFAs) have been recognized as important dietary compounds for infant and maternal nutrients, maintaining normal cardiovascular and immune system health, and for retarding the growth of tumor cells. The beneficial effects of these fatty acids can be obtained by eating fish several times a week or by daily intake of concentrated fish oil, which is available as a dietary source of omega-3 HUFAs.

There is a lot of interest in enriching the meat of poultry and swine with omega-3 HUFAs to provide consumers with additional dietary options for obtaining these nutritionally important fatty acids. It is well known that the omega-3 HUFA content of poultry and swine meat can be increased by including a source of these fatty acids in the feed of poultry and swine. Currently available sources of omega-3 HUFA for use in feed include fish oil and fish meal algae, flaxseed, rapeseed, soybeans, avocado meal, linseed oil and canola oil. Because these fatty acids are unstable and their oxidation products can lead to the development of off-flavor and odors in meat, they need to be added to the feed at low concentrations and in a stable form. Fish oil is notoriously unstable due to oxidation and recommendations exist regarding limiting its use in broiler rations to prevent development of off-flavor/odors. One could use highly refined/deodorized fish oils and/or microencapsulate them but both processes significantly increase the cost of the fish oil for use in feed and the deodorized oils are still readily susceptible to oxidation unless microencapsulated. Microalgae provide a source of stable, naturally encapsulated omega-3 HUFAs, but they are relatively expensive to grow in controlled conditions such as fermentors. Better quality, and better tasting omega-3 HUFA enriched meat could be produced if ways could be developed to effectively and economically use these more expensive sources of omega-3 HUFAs in the feed of poultry and swine. One of the most important improvements that could be made in this omega-3 HUFA enrichment process would be to find a way to significantly increase the incorporation efficiency of the omega-3 HUFAs in the feed into the resulting meat.

This would solve two key problems currently limiting the commercial production of omega-3 HUFA enriched meat: (1) high cost of production; and (2) taste and odor problems in the resulting meat. Less of the high quality omega-3 HUFA feed sources would be required to reach a target enrichment level thus significantly reducing the cost of the meats. Additionally, higher, more nutritionally beneficial concentration of omega-3 HUFAs could be achieved in meat if so desired without organoleptic compromise. Conversely, lower amounts of the lower quality, cheaper sources of omega-3 HUFAs (e.g. raw fish oil) could be used to achieve significant, but lower, enrichment levels without developing organoleptic problems in the meat.

SUMMARY OF THE INVENTION

The present invention provides a method for increasing the omega-3 HUFA incorporation efficiency in a poultry meat by feeding the poultry a higher amount of omega-3 HUFAs in the late phase of poultry's production period than in the early phase.

Preferably, the poultry is fed a majority of omega-3 HUFAs during the remaining productivity period after it has reached about sixty percent of its target weight, more preferably the poultry is fed at least about 60% of omega-3 HUFAs during the remaining productivity period after it has reached about sixty percent of its target weight, still more preferably the poultry is fed at least about 80% of omega-3 HUFAs during the remaining productivity period after it has reached about sixty percent of its target weight, and most preferably the poultry is fed substantially all omega-3 HUFAs during the remaining productivity period after it has reached about sixty percent of its target weight.

Alternatively, the poultry is fed a majority of omega-3 HUFAs during the final thirty percent of its productivity period, preferably the poultry is fed at least about 60% of omega-3 HUFAs during the final thirty percent of its productivity period, more preferably the poultry is fed at least about 80% of omega-3 HUFAs during the final thirty percent of its productivity period, and most preferably the poultry is fed substantially all of omega-3 HUFAs during the final thirty percent of its productivity period.

DETAILED DESCRIPTION OF THE INVENTION

As employed above and throughout this disclosure, the following terms, unless otherwise indicated, shall be understood to have the following meanings:

"Highly polyunsaturated fatty acid" or "HUFA" refers to a polyunsaturated fatty acid that is at least 20 carbon atoms in length.

"Incorporation efficiency" refers to the ratio of the amount of omega-3 HUFAs present in the poultry meat to the total amount of omega-3 HUFAs fed to the poultry.

"Incorporation efficiency rate" refers to the ratio of the amount of omega-3 HUFAs present in the poultry meat to the total amount of omega-3 HUFAs fed to the poultry over a given period.

"Feed rate" refers to the ratio of the amount of omega-3 HUFAs fed to a poultry in a given period.

"Feed omega-3 HUFA content" refers to the percentage, by weight, of an omega-3 HUFA source in the feed.

"Constant feed omega-3 HUFA content" refers to feeds in which feed omega-3 HUFA content is relatively equal. Preferably the variation of feed omega-3 HUFA content is less than about 2%, more preferably less than about 1%, and most preferably less than about 0.5%. It should be appreciated, however, that the exact amount of feed omega-3 HUFA content can vary slightly from one batch to another due to a variety of factors including a variability in the production process of the feed and a natural variability of the amount of omega-3 HUFAs present in the omega-3 HUFA source.

"Variable omega-3 HUFA content feeding regime" refers to a feeding regime in which the poultry is fed a feed which has a different feed omega-3 HUFA content at least once during the production period of the poultry.

"Low quality omega-3 HUFA source" refers to a source of omega-3 HUFAs which has at most only been partially refined to remove organoleptically related contaminants and break down products. A low quality omega-3 HUFA source may contain oxidized product of omega-3 HUFAs and/or free or alkylated amines, thereby imparting an undesirable odor or taste to the poultry which has been fed a sufficient amount of low quality omega-3 HUFAs. Exemplary low quality omega-3 HUFA sources include some fish oils and fish meals.

"Organoleptic" refers to undesirable taste and/or odors primarily due to break down products of omega-3 HUFAs such as aldehydes and ketones and/or break down products of proteins such as alkylated amines.

"Production period" refers to a time period from hatching of a poultry until its slaughter; therefore, it does not necessarily equal to the life expectancy of the animal.

"Poultry" refers to any avian species that is used as a food. Exemplary poultry include chickens, turkeys, cornish game hens, pheasants, quails, ducks, geese and pigeons. Preferably, poultry is selected from the group consisting of a chicken and turkey, and more preferably a broiler chicken. In the United States, a broiler chicken is a chicken raised for meat and has an average production period of about seven weeks. However, it should be appreciated that the broiler chicken in other countries may have a different production period. For example, a broiler chicken in some countries may have production period of from about 4 weeks to about 5 weeks, while a broiler chicken in other countries may have production period of from about 10 weeks to about 12 weeks. The length of the production period depends on the strain of broiler chicken and on the size of the bird desired by consumers in a particular country.

"Flavor rating" refers to a method of rating the flavor of a particular food by consumers using a given flavor rating scale.

The present invention provides a method for increasing the incorporation efficiency of omega-3 HUFAs in poultry meat. Specifically, the method of the present invention provides a poultry feeding regime which results in a higher incorporation efficiency of omega-3 HUFAs in the flesh of the poultry compared to a constant feed omega-3 HUFA content feeding regime, where the poultry is fed a constant feed omega-3 HUFA content throughout its production period. It should be appreciated that in a constant feed omega-3 HUFA content feeding regime, the percentage of omega-3 HUFA in the feed remains relatively constant throughout the production period.

The method of the present invention involves feeding a poultry a higher amount of omega-3 HUFAs in the later phase of the poultry's production period. Preferably, a majority of omega-3 HUFAs are fed to the poultry during the remaining productivity period after it has reached about sixty percent of its target weight, more preferably the poultry is fed at least about 60% of omega-3 HUFAs during the remaining productivity period after it has reached about sixty percent of its target weight, still more preferably the poultry is fed at least about 80% of omega-3 HUFAs during the remaining productivity period after it has reached about sixty percent of its target weight, and most preferably the poultry is fed substantially all omega-3 HUFAs during the remaining productivity period after it has reached about sixty percent of its target weight. Alternatively, the poultry is fed a majority of omega-3 HUFAs during its final thirty percent of the productivity period, preferably the poultry is fed at least about 60% of omega-3 HUFAs during its final thirty percent of the productivity period, more preferably the poultry is fed at least about 80% of omega-3 HUFAs during its final thirty percent of the productivity period, and most preferably the poultry is fed substantially all of omega-3 HUFAs during its final thirty percent of the productivity period.

The method of the present invention for increasing the incorporation efficiency of omega-3 HUFAs in poultry meat is generally used on poultry which are raised for its meat. The method of the present invention can also be used to increase the amount of omega-3 HUFAs in the meat of egg-laying poultry, such as hens, after their egg-producing period.

The method of the present invention provides at least about 50% higher omega-3 HUFA incorporation efficiency compared to any prior known feeding regime method using the same total amount of omega-3 HUFA during the production period, more preferably at least about 75%, still more preferably at least about 100%, and most preferably at least about 200%. Since the method of the present invention provides higher omega-3 HUFA incorporation efficiency compared to other prior known feeding regimes, the method of the present invention allows using a smaller total amount of omega-3 HUFAs than any prior known feeding regime to achieve the same amount of omega-3 HUFA incorporation in poultry meats. Alternatively, the method of the present invention provides poultry meats having a significantly higher amount of omega-3 HUFAs by using the same total amount of omega-3 HUFAs as prior known feeding regimes. Moreover, the increased omega-3 HUFA incorporation efficiency of the present invention may allow the use of some low quality omega-3 HUFA sources without undesirable effects on the meat such as odor and/or taste because these sources can be used in feed at lower concentrations or amounts.

Prior feeding regimes which utilize a fish-based omega-3 HUFA source, such as fish oil and/or fish meals, stop administering the feed containing a fish-based omega-3 HUFA source during the last about one or two weeks of the production period of the poultry to reduce the undesirable taste and/or odor of the poultry meat. In contrast, the method of the present invention allows the use of a fish-based omega-3 HUFA source during these time periods.

Omega-3 HUFAs in the feed refers to any ingredient which is known to contain omega-3 HUFAs, including isolated or concentrated omega-3 HUFAs. Exemplary ingredients which contain omega-3 HUFAs include marine organism-based sources such as fish, fish oils, krill, shrimps and macroalgae; microbial-based sources such as microalgae and bacteria; plant-based sources including genetically-engineered plants which produce omega-3 HUFAs; isolated omega-3 HUFAs; and encapsulated form of any of the above sources. Exemplary sources of omega-3 HUFA are disclosed in U.S. Pat. Nos. 5,656,319, 5,698,244 and 5,688,500, which are incorporated by reference herein in their entirety. Preferably a source of omega-3 HUFA is selected from the group consisting of microbial-based sources including microalgae and other microorganisms; fish; fish oils; fish meals; other residual biomass which contain omega-3 HUFAs; and mixtures thereof. More preferably the source of omega-3 HUFA is a microbial-based source. Still more preferably, the source of omega-3 HUFA is a microorganism of the order Thraustochytriales, even more preferably the source of omega-3 HUFAs is selected from the group consisting of microorganisms of genus Thraustochytrium, Schizochytrium and a mixture thereof, and most preferably from the group consisting of Schizochytrium sp. ATCC 20888, Schizochytrium sp. ATCC 20889 and a mixture thereof.

Although a source containing a precursor of omega-3 HUFAs, such as flaxseed, rapeseed, soybean, avocado meal, linseed oil and canola oil can be used in the feed, the method of the present invention generally does not provide a sufficient time period for a poultry to convert a significant amount of these precursors to omega-3 HUFAs.

It should be recognized that using a low quality omega-3 HUFA source such as some fish, fish meals or fish oils as a source of omega-3 HUFA may cause a strong fishy taste and/or odor often negatively affecting the taste of the feed and/or the meat. Therefore, when using a low quality omega-3 HUFA source, it is preferred that a sufficiently small amount is used to produce a poultry that exhibits meat flavor rating of within about 30% of the meat flavor rating of a poultry produced without an omega-3 HUFA source in their feed, more preferably within about 20%, still more preferably within about 10%, and most preferably within about 5%. In particular, when a low quality omega-3 HUFA source containing a fish oil is used, for example, it is preferred that the total amount of fish oil present in the feed is less than about 2%, more preferably less than about 1% and most preferably less than about 0.5%. Fish meals generally contain about 10% of fish oil.

The method of the present invention allows feeding the necessary amount of omega-3 HUFAs in a shorter period of time than prior feeding regimes to obtain a same level of omega-3 HUFA incorporation in the meat; therefore, the undesired effects on the meat from using an omega-3 HUFA source is further decreased by exposing the source of omega-3 HUFA for a shorter period in the generally high oxidation environment (for oil based ingredients) of pelletized or mash feeds.

Without being bound by any theory, it is believed that the method of the present invention increases the incorporation efficiency of the omega-3 HUFAs by providing the omega-3 HUFAs to the poultry during the period when it incorporates the omega-3 HUFAs more efficiently into its meat and by minimizing the time the omega-3 HUFA source spends in the feed (exposed to the oxidizing effects of air light and/or temperature), thereby reducing the amount of oxidation and providing more of the omega-3 HUFA source to the poultry.

The method of the present invention for increasing the incorporation efficiency of omega-3 HUFAs by a poultry involves subjecting the poultry to a variable omega-3 HUFA content feeding regime. The present method may also be used to increase the incorporation efficiency of omega-3 HUFAs in other animals which are suitable for human consumption including, but not limited to, domesticated animals such as cattle, swine, sheep and buffalo.

The amount of incorporation efficiency of omega-3 HUFAs by a poultry can be determined quantitatively by measuring the amount of omega-3 HUFAs in the feed and the poultry meat. A "meat" refers to any portion of the poultry which can incorporate the omega-3 HUFAs. Preferably, the meat is selected from the group consisting of fat, skin, organs, muscle, and marrow.

Additional objects, advantages, and novel features of this invention will become apparent to those skilled in the art upon examination of the following examples thereof, which are not intended to be limiting.

EXAMPLES

A typical growth and feed consumption of broiler chickens is shown in Table 1.

TABLE 1

Typical body weights and feed requirements of broiler chickens over a production cycle.

| Age | Body Wt. (g) | | Weekly feed consumption (g) | | Cumulative feed consumption (g) | |
|---|---|---|---|---|---|---|
| (weeks) | male | female | male | female | male | female |
| 1 | 152 | 144 | 135 | 131 | 135 | 131 |
| 2 | 376 | 344 | 290 | 273 | 425 | 404 |
| 3 | 686 | 617 | 487 | 444 | 912 | 848 |
| 4 | 1085 | 965 | 704 | 642 | 1616 | 1490 |
| 5 | 1576 | 1344 | 960 | 738 | 2576 | 2228 |
| 6 | 2088 | 1741 | 1141 | 1001 | 3717 | 3229 |
| 7 | 2590 | 2134 | 1281 | 1081 | 4998 | 4310 |

From Nutrient Requirements of Poultry, National Research Council (NRC), 9th Ed., National Academy Press, Washington, D.C., 1994.

Using these data, broiler chicken growth performance data are calculated and summarized in Table 2.

TABLE 2

Typical performance characteristics of broiler chickens calculated from the data in Table 1.

| Week | % Total Wt. Gain | | % Total Feed consumption | | Feed Conversion Ratio | |
|---|---|---|---|---|---|---|
| | male | female | male | female | male | female |
| 1–5 | 60.8 | 63.0 | 51.5 | 51.7 | 1.63 | 1.66 |
| 6–7 | 39.2 | 37.0 | 48.5 | 48.3 | 1.93 | 2.02 |

As can be seen in Table 2, a constant feed omega-3 content feeding regime would provide approximately 50% of the amount of omega-3 HUFAs during the first 5 weeks of growth and approximately 50% in the last two weeks of growth. The broiler chickens complete about 60% of their growth in the first 5 weeks of growth and their feed conversion is significantly higher during this time period compared to the last two weeks of growth. A "feed conversion" refers to a ratio of feed consumption to body weight, and hence is a rough estimate of the broiler chicken's efficiency in utilizing the feed to increase the body weight.

Example 1

This example illustrates omega-3 HUFA incorporation efficiency of a feeding regime using a constant feed omega-3 HUFA content.

Two thousand two hundred and forty broiler chickens were sexed at day of hatch and randomly assigned to one of four dietary treatments. Three of the treatments (broiler rations formulated to meet NRC requirements (NRC, 1994)) provided DHA (docosahexaenoic acid, C22:6n-3) in the form of dried Schizochytrium sp. (17.5% DHA as % dry weight) at the following concentrations: 0.09%, 0.27% and 0.45% of weight. The fourth treatment was a control broiler ration meeting NRC requirements but containing no source of DHA. Each dietary treatment contained 560 broilers divided among eight replicates (n=70; 35 males, 35 females). The feed was fed to the birds under the standard 3-phase feeding program: starter (day 0–21); grower (day 22–42); and finisher (day 43–49). All rations were pelletized prior to feeding to the birds. The concentration in each ration was verified by gas chromatography. At the end of 49 days, two birds (one male, one female) from each replicate were sacrificed and the DHA content of the meat (skinless) was determined as fatty acid methyl esters by gas chromatography. The results are presented in Table 3. Enrichment of all three highly unsaturated omega-3 fatty acids (DHA, docosahexaenoic acid, C22:6n-3; DPA, docosapentaenoic acid, C22:5n-3; and EPA, eicosapentaenoic acid, C20:5n-3) was observed. As a point of comparison, DHA concentrations in the resulting breast meat were 17, 31, 64 and 71 mg/100 g respectively for the 0.0, 0.09, 0.27, and 0.45% DHA levels in the feed.

12.8% dry weight. At the end of the 49 day production cycle, 10 birds from each treatment were randomly collected, sacrificed, processed and then frozen. Freeze dried samples of the breast meat were then analyzed for their DHA content by gas chromatography. The enrichment levels of DHA and total omega-3 highly unsaturated fatty acids are summarized in Table 4.

TABLE 4

Long chain omega-3 HUFA enrichment levels obtained in broiler chickens when the chickens were fed all of the DHA for enrichment purposes during the last 14 days of the 49 day production cycle. Data are means and standard deviations of ten breasts per treatment.

| Tot. Amt. | | | Long Chain Omega-3 Content | | |
|---|---|---|---|---|---|
| DHA Fed (g) | Enrichment Strategy[1] | Meat Sample | DHAn-3 (mg/100 g) | Total LCn-3 (mg/100 g) | n-6/n-3 ratio |
| 0 | 0%/0% | breast | 16.7 ± 1.7 | 27.7 ± 3.3 | 14.5 |
| 3.6 | 100%/0% | breast | 52.8 ± 2.6 | 58.0 ± 2.8 | 3.6 |
| 3.6 | 85%/15% | breast | 77.4 ± 5.5 | 88.1 ± 5.3 | 2.8 |
| 3.6 | 67%/33% | breast | 51.8 ± 4.8 | 62.2 ± 8.0 | 4.6 |

TABLE 3

Omega-3 HUFA enrichment levels obtained in broiler chickens when the chickens were fed a fixed amount of DHA as % of their ration over the entire production cycle. Data are means and standard deviations of four breasts and thighs from each treatment.

| | | | Long Chain omega-3 HUFA Content | | | |
|---|---|---|---|---|---|---|
| DHA Amt. In Feed Ration | Total Amt. DHA Fed (g)[1] | Meat Sample | DHAn-3 (mg/100 g) | DPAn-3 (mg/100 g) | EPAn-3 (mg/100 g) | Total LCn-3 (mg/100 g) |
| 0.00% | 0 | breast | 16.6 ± 11.0 | 5.0 ± 0.6 | 0 ± 0 | 21.6 |
| | | thigh | 16.8 ± 12.7 | 4.4 ± 0.1 | 0.1 ± 0.2 | 21.3 |
| 0.09% | 4 | breast | 31.1 ± 3.6 | 5.2 ± 0.2 | 0 ± 0 | 36.3 |
| | | thigh | 30.0 ± 1.6 | 5.9 ± 0.9 | 0.3 ± 0.3 | 36.5 |
| 0.27% | 12 | breast | 63.9 ± 1.1 | 6.5 ± 0.4 | 0 ± 0 | 70.4 |
| | | thigh | 58.4 ± 9.1 | 7.9 ± 0.1 | 0.6 ± 0.4 | 66.9 |
| 0.45% | 20 | breast | 70.7 ± 5.6 | 7.0 ± 1.3 | 0 ± 0 | 77.7 |
| | | thigh | 92.1 ± 13.0 | 9.7 ± 1.1 | 1.5 ± 0.4 | 103.3 |

[1]Total grams of DHA fed to the broiler chickens over 49 days

Example 2

This example illustrate omega-3 HUFA incorporation efficiency using a variable omega-3 content feeding regime.

Two thousand, five hundred broiler chickens (birds not sexed at time of placement) were placed in 50 commercial production pens, 50 birds per pen. Ten pens were randomly assigned to the control treatment and 8 pens were randomly assigned to each of the 5 treatments. The treatments consisted of 5 variable feeding regimes, 4 of which provided a total of 3.6 g of DHA and one of which provided a total of 5 g of DHA to the birds during the last 14 days of their 49 day production cycle. The variable feed rate treatments (% total DHA fed over day 36–43/% total DHA fed over day 44–49) were as follows: 4 g of total DHA as 100%/0%; 85%/15%; 67%/33%; 50%/50%; and 5 g of total DHA as 67%/33%. There was also one control treatment in which the broiler chickens were fed a ration without any DHA. All diets were commercially formulated broiler feeds and were isocaloric and isonitrogenous within each feeding period (starter, grower, and finisher). All rations were pelletized prior to feeding to the birds. DHA was provided in the rations as dried Schizochytrium sp. with a DHA content of TABLE 4-continued Long chain omega-3 HUFA enrichment levels obtained in broiler chickens when the chickens were fed all of the DHA for enrichment purposes during the last 14 days of the 49 day production cycle. Data are means and standard deviations of ten breasts per treatment.

| Tot. Amt. | | | Long Chain Omega-3 Content | | |
|---|---|---|---|---|---|
| DHA Fed (g) | Enrichment Strategy[1] | Meat Sample | DHAn-3 (mg/100 g) | Total LCn-3 (mg/100 g) | n-6/n-3 ratio |
| 3.6 | 50%/50% | breast | 66.0 ± 4.4 | 72.3 ± 4.7 | 3.2 |
| 5.0 | 67%/33% | breast | 79.0 ± 3.7 | 92.2 ± 5.4 | 3.0 |

[1]Enrichment strategy = % total DHA fed over day 36–43/% total DHA fed over day 44–49.

DHA contents of the breast meat ranged from 52–77 mg/100 g breast meat for the treatments providing 3.6 g total DHA and 79 mg for the single treatment containing 5 g total DHA. Normalized to the 4 g dose used in Example 1, these results represent DHA contents of the breast meat in the range of about 58–86 mg/100 g breast meat.

It should also be noted that the incorporation efficiency is still approximately linear in the range evaluated in this Example (e.g. 3.6 g @ 67%/33%=52 mg DHA/100 g breast meat vs. 5.0 g DHA @ 67%/33%=79 mg DHA/100 g breast meat) as compared to the inverse exponential response (much less efficient response) observed in Example 1 utilizing a constant rate feeding strategy.

Those skilled in the art will appreciate that numerous changes and modifications may be made to the preferred embodiments of the invention and that such changes and modifications may be made without departing from the spirit and scope of the invention. It is therefore intended that the appended claims cover all such equivalent variations as fall within the true spirit and scope of the invention.

What is claimed is:

1. A method for increasing the amount of an omega-3 highly unsaturated fatty acid in the meat of poultry comprising feeding a feed to said poultry, wherein said feed comprises a source of said omega-3 highly unsaturated fatty acid, and wherein the percentage of omega-3 highly unsaturated fatty acid in said feed is higher in a later phase of said poultry's production period than in an earlier phase; and wherein an amount of any low quality omega-3 highly unsaturated fatty acid source oil is less than 2 percent by weight of the feed.

2. The method of claim 1, wherein said source of said omega-3 highly unsaturated fatty acid is selected from the group consisting of marine organism-based sources, microbial-based sources, and plant-based sources.

3. The method of claim 1, wherein said source of said omega-3 highly unsaturated fatty acid is selected from the group consisting of algae, fish oil, fish meal and mixtures thereof.

4. The method of claim 1, wherein said source of said omega-3 highly unsaturated fatty acid is a marine microorganism.

5. The method of claim 1, wherein said source of said omega-3 fatty acid is a microorganism of the order Thraustochytriales.

6. The method of claim 1, wherein said low quality omega-3 highly unsaturated fatty acid source is fish oil, fish meal or other residual biomass from which omega-3 highly unsaturated fatty acid has been extracted.

7. The method of claim 1, wherein said poultry is fed a majority of said source of said omega-3 highly unsaturated fatty acid after said poultry reaches about sixty percent of its target weight.

8. The method of claim 1, wherein said poultry is fed at least about 60% of said source of said omega-3 highly unsaturated fatty acid after said poultry reaches about sixty percent of its target weight.

9. The method of claim 1, wherein said poultry is fed at least about 80% of said source of said omega-3 highly unsaturated fatty acid after said poultry reaches about sixty percent of its target weight.

10. The method of claim 1, wherein said poultry is fed substantially all of said source of said omega-3 highly unsaturated fatty acid after said poultry reaches about sixty percent of its target weight.

11. The method of claim 1, wherein said poultry is fed a majority of said source of said omega-3 highly unsaturated fatty acid during about the final thirty percent of said poultry's production period.

12. The method of claim 1, wherein said poultry is fed at least about 60% of said source of said omega-3 highly unsaturated fatty acid during about the final thirty percent of said poultry's production period.

13. The method of claim 1, wherein said poultry is fed at least about 80% of said source of said omega-3 highly unsaturated fatty acid during about the final thirty percent of said poultry's production period.

14. The method of claim 1, wherein said poultry is fed substantially all of said source of said omega-3 highly unsaturated fatty acid during about the final thirty percent of said poultry's production period.

15. The method of claim 1, wherein the amount of omega-3 highly unsaturated fatty acid concentration in the meat of said poultry is at least about 50 percent higher than the meat of a control poultry which has been fed the same total amount of said source of omega-3 highly unsaturated fatty acid but at a relatively constant feed omega-3 highly unsaturated fatty acid content during the substantially similar production period of said poultry.

16. The method of claim 1, wherein said poultry is selected from the group consisting of chickens and turkeys.

17. The method of claim 1, wherein said poultry is a broiler chicken.

18. The method of claim 1, wherein said omega-3 highly unsaturated fatty acid is DHA.

19. The method of claim 1, wherein the total amount of said DHA fed to said poultry during the production period of said poultry is at least about 0.5 g.

20. The method of claim 1, wherein the breast meat of said poultry contains at least about 25 mg of DHA per 100 g of the breast meat.

21. The method of claim 1, wherein the thigh meat of said poultry contains at least about 25 mg of DHA per 100 g of the thigh meat.

22. The method of claim 1, wherein said poultry is fed substantially all of said source of said omega-3 highly unsaturated fatty acid during about the final two weeks of said poultry's production period.

23. The method of claim 1, wherein said poultry is fed substantially all of said source of said omega-3 highly unsaturated fatty acid during the period in which the last about 50% of said poultry's total feed is consumed.

24. The method of claim 1, wherein oxidation of said source of omega-3 highly unsaturated fatty acid is kept desirably low by minimizing the exposure time of said source of said omega-3 highly unsaturated fatty acid to oxidative conditions.

25. The method of claim 1, wherein said meat of said poultry includes fat, skin, organs, muscle and marrow.

26. A method for increasing the amount of omega-3 highly unsaturated fatty acid in the meat of poultry comprising feeding a feed to said poultry, wherein said feed comprises a source of said omega-3 highly unsaturated fatty acid, and wherein the percentage of omega-3 highly unsaturated fatty acid in said feed is higher in a later phase of said poultry's production period than in an earlier phase; and wherein the amount of low quality omega-3 highly unsaturated fatty acid source which is fed to said poultry is limited to an amount which provides poultry with meat flavor rating of within about 30% of the meat flavor rating of poultry produced without said source of said omega-3 highly unsaturated fatty acid in said feed.

27. The method of claim 26, wherein said source of said omega-3 highly unsaturated fatty acid is selected from the group consisting of algae, fish oil, fish meal and mixtures thereof.

28. The method of claim 26, wherein said source of said omega-3 fatty acid is a microorganism of the order Thraustochytriales.

29. The method of claim 26, wherein said low quality omega-3 highly unsaturated fatty acid source is fish oil, fish meal or other residual biomass from which omega-3 highly unsaturated fatty acid has been extracted.

30. The method of claim 26, wherein said poultry is fed at least about 80% of said source of said omega-3 highly unsaturated fatty acid after said poultry reaches about sixty percent of its target weight.

31. The method of claim 26, wherein said poultry is fed substantially all of said source of said omega-3 highly unsaturated fatty acid after said poultry reaches about sixty percent of its target weight.

32. The method of claim 26, wherein said poultry is fed at least about 80% of said source of said omega-3 highly unsaturated fatty acid during about the final thirty percent of said poultry's production period.

33. The method of claim 26, wherein said poultry is fed substantially all of said source of said omega-3 highly unsaturated fatty acid during about the final thirty percent of said poultry's production period.

34. The method of claim 26, wherein the amount of omega-3 highly unsaturated fatty acid concentration in the meat of said poultry is at least about 50 percent higher than the meat of a control poultry which has been fed the same total amount of said source of omega-3 highly unsaturated fatty acid but at a relatively constant feed omega-3 highly unsaturated fatty acid content during the substantially similar production period of said poultry.

35. The method of claim 26, wherein said poultry is selected from the group consisting of chickens and turkeys.

36. The method of claim 26, wherein said poultry is a broiler chicken.

37. The method of claim 26, wherein said omega-3 highly unsaturated fatty acid is DHA.

38. The method of claim 26, wherein the total amount of said DHA fed to said poultry during the life or growth cycle of said poultry is at least about 0.5 g.

39. The method of claim 26, wherein the breast meat of said poultry contains at least about 25 mg of DHA per 100 g of the breast meat.

40. The method of claim 26, wherein the thigh meat of said poultry contains at least about 25 mg of DHA per 100 g of the thigh meat.

41. The method of claim 26, wherein said poultry is fed substantially all of said source of said omega-3 highly unsaturated fatty acid during about the final two weeks of said poultry's production period.

42. The method of claim 26, wherein said poultry is fed substantially all of said source of said omega-3 highly unsaturated fatty acid during the period in which the last about 50% of said poultry's total feed is consumed.

43. The method of claim 26, wherein oxidation of said source of omega-3 highly unsaturated fatty acid is kept desirably low by minimizing the exposure time of said source of said omega-3 highly unsaturated fatty acid to oxidative conditions.

44. The method of claim 26, wherein said meat of said poultry includes fat, skin, organs, muscle and marrow.

45. A method for increasing the amount of an omega-3 highly unsaturated fatty acid in the meat of poultry comprising feeding a feed to said poultry, wherein said feed comprises a source of said omega-3 highly unsaturated fatty acid, and wherein the percentage of omega-3 highly unsaturated fatty acid in said feed is higher in a later phase of said poultry's production period than in an earlier phase; and
  wherein the incorporation efficiency is at least 50 percent greater than the incorporation efficiency of any prior known poultry feeding protocol for increasing the amount of an omega-3 highly unsaturated fatty acid in the meat of poultry.

46. The method of claim 45, wherein the incorporation efficiency is at least 75 percent greater than the incorporation efficiency of any prior known poultry feeding protocol for increasing the amount of an omega-3 highly unsaturated fatty acid in the meat of poultry.

47. The method of claim 45, wherein the incorporation efficiency is at least 100 percent greater than the incorporation efficiency of any prior known poultry feeding protocol for increasing the amount of an omega-3 highly unsaturated fatty acid in the meat of poultry.

48. The method of claim 45, wherein the incorporation efficiency is at least 200 percent greater than the incorporation efficiency of any prior known poultry feeding protocol for increasing the amount of an omega-3 highly unsaturated fatty acid in the meat of poultry.

49. The method of claim 45, wherein said source of said omega-3 highly unsaturated fatty acid is selected from the group consisting of algae, fish oil, fish meal and mixtures thereof.

50. The method of claim 45, wherein said source of said omega-3 fatty acid is a microorganism of the order Thraustochytriales.

51. The method of claim 45, wherein said low quality omega-3 highly unsaturated fatty acid source is fish oil, fish meal or other residual biomass from which omega-3 highly unsaturated fatty acid has been extracted.

52. The method of claim 45, wherein said poultry is fed at least about 80% of said source of said omega-3 highly unsaturated fatty acid after said poultry reaches about sixty percent of its target weight.

53. The method of claim 45, wherein said poultry is fed substantially all of said source of said omega-3 highly unsaturated fatty acid after said poultry reaches about sixty percent of its target weight.

54. The method of claim 45, wherein said poultry is fed at least about 80% of said source of said omega-3 highly unsaturated fatty acid during about the final thirty percent of said poultry's production period.

55. The method of claim 45, wherein said poultry is fed substantially all of said source of said omega-3 highly unsaturated fatty acid during about the final thirty percent of said poultry's production period.

56. The method of claim 45, wherein said omega-3 highly unsaturated fatty acid is DHA.

57. The method of claim 45, wherein the total amount of said DHA fed to said poultry during the life or growth cycle of said poultry is at least about 0.5 g.

58. The method of claim 45, wherein said poultry is fed substantially all of said source of said omega-3 highly unsaturated fatty acid during about the final two weeks of said poultry's production period.

59. The method of claim 45, wherein said poultry is fed substantially all of said source of said omega-3 highly unsaturated fatty acid during the period in which the last about 50% of said poultry's total feed is consumed.

60. The method of claim 45, wherein oxidation of said source of omega-3 highly unsaturated fatty acid is kept desirably low by minimizing the exposure time of said source of said omega-3 highly unsaturated fatty acid to oxidative conditions.

61. The method of claim 45, wherein said meat of said poultry includes fat, skin, organs, muscle and marrow.

62. A method for increasing the uptake of an omega-3 highly unsaturated fatty acid by an animal relative to a constant ratio feeding protocol, wherein said constant ratio feeding protocol comprises feeding said animal during said animal's production period a constant level feed which comprises a substantially constant level of a source of said omega-3 highly unsaturated fatty acid, comprising:

(a) feeding said animal a variable feed such that the level of said source of said omega-3 highly unsaturated fatty acid in said variable feed varies during the production period of said animal, wherein said variable feed comprises said source of said omega-3 highly unsaturated fatty acid, and wherein the total amount of said source of said omega-3 highly unsaturated fatty acid fed to said animal during the production period of said animal is substantially equal to the total amount of said source of said omega-3 highly unsaturated fatty acid fed to said animal during said animal's production period using said constant ratio feeding protocol;

(b) analyzing the meat of said animal in order to determine the level of omega-3 highly unsaturated fatty acid in said meat; and (c) devising a variable ratio feeding protocol for said animal based on the amount of said omega-3 highly unsaturated fatty acid uptake determined by step (b) in order to substantially increase the uptake of said omega-3 highly unsaturated fatty acid by said animal relative to said constant ratio feeding protocol.

63. The method of claim 62, wherein said variable ratio feeding protocol results in at least about 50% increase in said omega-3 highly unsaturated fatty acid concentration in the meat of said animal relative to the concentration of said omega-3 highly unsaturated fatty acid in the meat of said animal which has been fed a substantially equal total amount of said omega-3 highly unsaturated fatty acid using said constant ratio feeding protocol.

64. The method of claim 62, wherein said variable ratio feeding protocol utilizes less than about 50% of the total amount of said source of said omega-3 highly unsaturated fatty acid compared to said constant ratio feeding protocol to achieve a substantially similar concentration of said omega-3 highly unsaturated fatty acid in the meat of said animal.

65. A method of feeding poultry, comprising feeding said poultry at least about fifty percent of the total amount of a source of an omega-3 highly unsaturated fatty acid to said poultry during the final thirty percent of said poultry's production period.

66. The method of claim 65, wherein the source of said omega-3 highly unsaturated fatty acid is selected from the group consisting of algae, fish oil, fish meal and mixtures thereof.

67. The method of claim 65, wherein the source of said omega-3 highly unsaturated fatty acid comprises a microorganism of the order Thraustochytriales.

68. The method of claim 65, wherein said poultry is fed substantially all of the total amount of said source of said omega-3 highly unsaturated fatty acid during the final thirty percent of said poultry's production period or during the portion of the production period in which said poultry gains the final forty percent of a target weight.

69. The method of claim 65, wherein the total amount of said omega-3 highly unsaturated fatty acid fed to said poultry during the final thirty percent of said poultry's production period or during the portion of the production period in which said poultry gains the final forty percent of target weight is at least about 0.5 g.

70. The method of claim 1, wherein the amount of any low quality omega-3 highly unsaturated fatty acid source oil is less than 1 percent by weight of the feed.

71. The method of claim 26, wherein the amount of any low quality omega-3 highly unsaturated fatty acid source oil is less than 1 percent by weight of the feed.

72. The method of claim 45, wherein the amount of any low quality omega-3 highly unsaturated fatty acid source oil is less than 1 percent by weight of the feed.

73. The method of claim 65, wherein an amount of any low quality omega-3 highly unsaturated fatty acid source oil is less than 1 percent by weight of the feed.

* * * * *